United States Patent [19]
Nakamura et al.

[11] Patent Number: 6,147,252
[45] Date of Patent: Nov. 14, 2000

[54] PROCESS FOR CONTINUOUSLY PRODUCING ESTER OF ACRYLIC OR METHACRYLIC ACID

[75] Inventors: Kenichi Nakamura; Futoshi Kawataka, both of Ibaraki-ken, Japan

[73] Assignee: Mitsubishi Gas Chemical Company, Inc., Tokyo, Japan

[21] Appl. No.: 09/343,222

[22] Filed: Jun. 30, 1999

[30] Foreign Application Priority Data

Jul. 1, 1998 [JP] Japan .................................. 10-185827

[51] Int. Cl.$^7$ .................................................. C07C 67/02
[52] U.S. Cl. ............................................................ 560/217
[58] Field of Search ............................................ 560/217

[56] References Cited

U.S. PATENT DOCUMENTS 3,686,268  8/1972  Jobert et al. .
4,202,990  5/1980  Murakami et al. .

FOREIGN PATENT DOCUMENTS

040724 A1  12/1981  European Pat. Off. .
640583 A2  3/1995  European Pat. Off. .
640583 A3  3/1995  European Pat. Off. .
50-19716  3/1975  Japan .
52-111512  9/1977  Japan .
62-42948  2/1987  Japan .
6-293702  10/1994  Japan .
960005  6/1964  United Kingdom .

*Primary Examiner*—Joseph K. McKane
*Assistant Examiner*—Joseph Murray
*Attorney, Agent, or Firm*—Antonelli, Terry, Stout & Kraus, LLP

[57] ABSTRACT

A process for continuously producing an alkyl ester of acrylic or methacrylic acid by ester interchange reaction represented by the following reaction scheme:

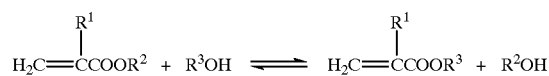

wherein $R^1$ is hydrogen or methyl, $R^2$ is an alkyl having 1 to 6 carbon atoms, $R^3$ is an alkyl having 2 to 20 carbon atoms or a mono- or polyhydroxyalkyl having 2 to 20 carbon atoms such that $R^2OH$ has a boiling point lower than that of $R^3OH$. The reaction is continuously carried out in a continuous multi-stage distillation column while simultaneously removing the low-boiling $R^2OH$ from the reaction zone by distillation, thereby shifting the equilibrium toward the product side to enhance the production of the target alkyl ester.

13 Claims, 1 Drawing Sheet

PROCESS FOR CONTINUOUSLY PRODUCING ESTER OF ACRYLIC OR METHACRYLIC ACID

BACKGROUND OF THE INVENTION

1. Field of the Invention

The present invention relates to a process for continuously producing an alkyl ester of acrylic or methacrylic acid by ester interchange reaction between a starting alkyl ester of acrylic or methacrylic acid and a starting alcohol.

Hereinafter, for clarity and easiness purposes, the starting alkyl ester of acrylic or methacrylic acid may be referred to as "alkyl ester (A)," the starting alcohol may be referred to as "alcohol (B)," the resulting intended alkyl ester of acrylic or methacrylic acid may be referred to as "alkyl ester (C)" and a by-produced alcohol may be referred to as "alcohol (D)."

2. Description of the Related Art

It is known that an alkyl ester of acrylic or methacrylic acid can be produced by ester interchange reaction. The ester interchange reaction is an equilibrium reaction and various catalysts have been proposed to increase the reaction rate. Examples of the proposed catalysts include acids such as sulfuric acid and p-toluenesulfonic acid (Japanese Patent Application Laid-Open No. 62-42948), basic substances such as alcoholates, hydroxides, carbonates, phosphates, oxides and complexes of alkali metals and alkaline earth metals (Japanese Patent Application Laid-Open Nos. 53-144523, 55-27118, 56-77242, 57-93930, 62-185051, 63-5054, 63-5055, 2-104559, 2-193944 and 6-293702), metal alcoholates such as aluminum alcoholates and magnesium alcoholates (Japanese Patent Application Laid-Open No. 50-19716), titanium compounds such as titanium alcoholates, titanium phenoxide and alkyltitaniums (Ger Offene 2319688, U.S. Pat. No. 3,686,268 and Japanese Patent Application Laid-Open No. 1-258642) and lead compounds, zinc compounds, tin compounds and complexes of metals such as copper, iron and zirconium (Japanese Patent Application Laid-Open Nos. 53-141213 and 53-105417 and U.S. Pat. No. 4,202,990). Further, a process using a metal or a metal oxide as the catalyst has been proposed (Japanese Patent Application Laid-Open No. 52-111512).

In the proposed process, a reaction apparatus having a distillation column, a fractionating column, etc. at an upper position of a reaction vessel is preferably used so that a lower alcohol by-produced in a batch process is separated from the remaining starting mixture, the reaction product and the solvent by distillation. It is apparent that the ester interchange reaction takes place only in a reaction vessel containing a catalyst. The distillation column, etc. disposed at an upper position of the reaction vessel is used only to separate the lower alcohol by-produced in the ester interchange reaction from the other components in the reaction vessel. Therefore, in the proposed consecutive process of the reaction and distillation, the ester interchange reaction and the distillation are conducted at the separate portions in the reaction apparatus. Namely, in the distillation column, only the distillation is carried out and the ester interchange reaction does not occur therein. In such a process, the ester interchange reaction, which is conducted in the liquid phase in the reaction vessel, proceeds only when the equilibrium of the reaction is shifted toward the product side by the moving of the by-produced low-boiling alcohol from liquid phase to vapor phase through the vapor-liquid interface. Since the reaction vessel used in the conventional process is a tank having a vapor-liquid interface area as small as the cross-sectional area of the tank, it is known that the ester interchange reaction proceeds very slowly. For example, the batch process takes a reaction time as long as 2 to 5 hours to obtain a sufficient result. The conventional process further requires a high reaction temperature to obtain a sufficient reaction rate. The high reaction temperature occasionally decreases the selectivity of the intended alkyl ester (C) due to disadvantageous side reactions such as the polymerization of the starting alkyl ester (A) or the resulting alkyl ester (C) and the addition reaction of the alcohol to the double bond of the alkyl esters (A) and (C).

In the conventional process conducting the ester interchange reaction and the distillation at the separate portions in the apparatus, the ester interchange reaction is carried out in a batch process by placing the alkyl ester (A), the alcohol (B) and a catalyst in a reaction vessel, and then, allowing the ester interchange reaction to take place. Thus, no continuous process, in which the starting materials are supplied continuously and the products are taken out continuously, has been proposed in the production of an alkyl ester of acrylic or methacrylic acid.

SUMMARY OF THE INVENTION

Accordingly, an object of the present invention is to overcome the above problems in the conventional process and to provide a process for continuously producing the alkyl ester (C) of acrylic or methacrylic acid with a high reaction rate and a high selectivity.

As a result of intense research on the production of the alkyl ester (C) of acrylic or methacrylic acid by ester interchange reaction between the alkyl ester (A) of acrylic or methacrylic acid and the alcohol (B) in the presence of a catalyst, the inventors have found that the above object can be achieved easily by continuously conducting the ester interchange reaction in a continuous multi-stage distillation column while simultaneously distilling off the by-produced alcohol (D). The present invention has been accomplished based on this finding.

Thus, the present invention provides a process for continuously producing an alkyl ester of acrylic or methacrylic acid by ester interchange reaction represented by the following reaction scheme:

wherein $R^1$ is hydrogen or methyl, $R^2$ is an alkyl having 1 to 6 carbon atoms, $R^3$ is an alkyl having 2 to 20 carbon atoms or a mono- or polyhydroxyalkyl having 2 to 20 carbon atoms such that $R^2OH$ has a boiling point lower than that of $R^3OH$, the process comprising the steps of (1) supplying the starting alkyl ester:

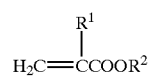

and the starting alcohol $R^3OH$ to a continuous multi-stage distillation column as starting materials; (2) bringing the starting materials into contact with a catalyst in the distillation column to allow the ester interchange reaction to take place between the starting materials while continuously taking out the by-produced alcohol $R^2OH$ in a vapor form by distillation; and (3) continuously taking out the resultant alkyl ester of acrylic or methacrylic acid:

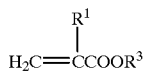

in a liquid form from a lower position of the distillation column.

DESCRIPTION OF THE PREFERRED EMBODIMENTS

Figure 1:
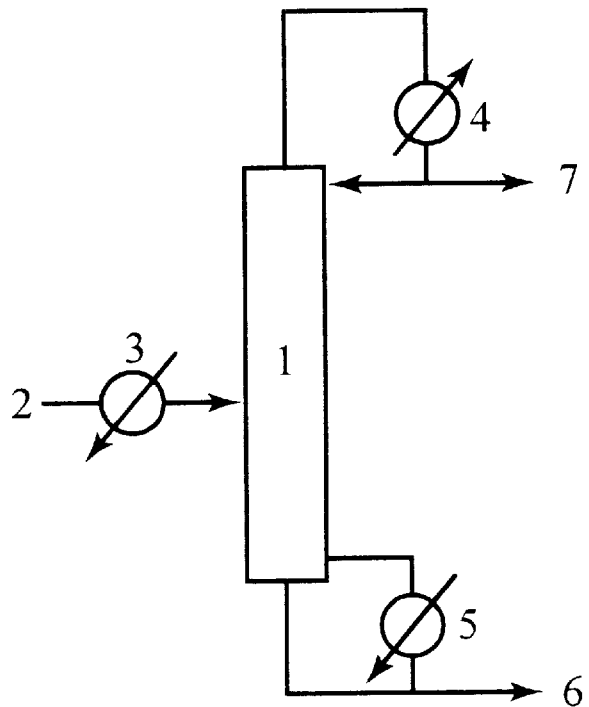
FIG. 1 is a flow sheet showing a process of the present invention where the starting materials are introduced together into the same stage of a continuous multi-stage distillation column.

In the present invention, the ester interchange reaction is represented by the following reaction scheme:

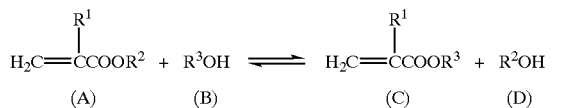

wherein $R^1$ is hydrogen or methyl, $R^2$ is an alkyl having 1 to 6 carbon atoms, $R^3$ is an alkyl having 2 to 20 carbon atoms or a mono- or polyhydroxyalkyl having 2 to 20 carbon atoms such that $R^2OH$ has a boiling point lower than that of $R^3OH$.

The starting alkyl ester (A) is an acrylic or methacrylic ester. $R^2$ constituting the ester moiety of the alkyl ester (A) is an alkyl having 1 to 6 carbon atoms, preferably 1 to 3 carbon atoms, and more preferably methyl or ethyl. The starting alcohol (B) represented by $R^3OH$ is a monohydric alcohol or a polyhydric alcohol having 2 or more hydroxyl groups. $R^3$ is a straight, branched or cyclic alkyl having 2 to 20, preferably 2 to 10 carbon atoms, or a straight, branched or cyclic mono- or polyhydroxyalkyl having 2 to 20, preferably 2 to 6 carbon atoms. Examples of the alcohol (B) include ethanol, 1-propanol, 2-propanol, 1-butanol, 2-butanol, t-butanol, 2-ethylhexanol, lauryl alcohol, stearyl alcohol, cyclohexyl alcohol, ethylene glycol, triethylene glycol, tetraethylene glycol, 1,3-butanediol and trimethylolpropane. The stating alkyl ester (A) and the starting alcohol (B) are selected so that the by-produced alcohol (D) represented by $R^2OH$ has a boiling point lower that that of the starting alcohol (B).

In the present invention, any catalyst may be used so long as the catalyst catalyzes the ester interchange reaction between the alkyl ester (A) and the alcohol (B) to efficiently provide the intended alkyl ester (C). Examples of the catalyst include acids such as sulfuric acid and p-toluenesulfonic acid; basic substances such as alcoholates, hydroxides, carbonates, phosphates, oxides and complexes of alkali metals or alkaline earth metals; metal alcoholates such as aluminum alcoholates and magnesium alcoholates; titanium compounds such as titanium alcoholates, titanium phenoxide and alkyltitaniums; compounds of lead, zinc or tin; and complexes of copper, iron or zirconium. Further examples of the catalyst include metals, metal oxides and crystalline solid acids, and these solid catalysts may be modified at the surface. The catalyst may be soluble or insoluble in the reaction solution under the reaction conditions. The catalyst may be mixed with or supported on a compound inert to the reaction. The catalyst may react with organic compounds present in the reaction system such as alcohols, acrylic or methacrylic acid, alkyl esters of acrylic or methacrylic acid or phenols generally used as the polymerization inhibitor to form a modified catalyst. Also, the catalyst may be heat-treated with the starting materials or the reaction products before being used in the reaction. Of the above catalysts, titanium compounds such as esters of titanic acid, titanium alcoholates, titanium phenoxide and alkyltitaniums are preferably used. Particularly preferred is a titanium complex resulted from the reaction of these titanium compounds with the organic compounds in the reaction system or a titanium complex formed by heat-treating these titanium compounds with the starting materials or the reaction products prior to use in the reaction.

The ester interchange reaction is carried out preferably in the presence of a polymerization inhibitor because the reaction includes the compounds easily polymerizable. Typical examples of the polymerization inhibitor include hydroquinone, hydroquinone monomethyl ether, di-t-butylcatechol, phenothiazine, p-phenylenediamine and methylene blue. The amount of the polymerization inhibitor is preferably 10 ppm to 10% by weight of the alkyl ester (A).

In the present invention, any continuous multi-stage distillation column may be used so long as the distillation column has two or more distillation stages and the distillation can be carried out continuously. In the present invention, the number of distillation stages of the distillation column means the number of plates in the case of a plate distillation column and the number of theoretical distillation stages in the case of a packed distillation column. Examples of the multi-stage distillation column include a plate distillation column using trays such as bubble-cap trays, perforated plate trays, valve trays and counterflow trays, and a packed distillation column packed with a packing such as Raschig ring, Lessing ring, pall ring, Berl saddle, intalox saddle, Dickson packing, McMahon packing, helipack, Sleuser packing and mellapack. Any other distillation columns generally used in a continuous process as a multi-stage distillation column may be used. A distillation column having a combination of a plate portion and a packed portion is also preferably used. Further, a packed distillation column packed partially or entirely with a solid catalyst may be used.

The ester interchange reaction is an equilibrium reaction generally carried out in a liquid phase. The process of the present invention is characterized by carrying out the ester interchange reaction in a reaction-distillation column Namely, the ester interchange reaction is carried out in a continuous multi-stage distillation column in the presence of the catalyst, preferably at a plurality of stages in the presence of the catalyst while simultaneously removing the low-boiling lower alcohol by-produced in the course of the reaction from the reaction system by distillation. The continuous production of the intended alkyl ester (C) of acrylic or methacrylic acid with a great yield and a high selectivity has been first achieved by such a process.

The greater reaction rate and the increased yield and selectivity of the process of the present invention as compared with those in the conventional process may be accounted for as follows. Since the ester interchange reaction is an equilibrium reaction, the low-boiling product (substantially the lower alcohol (D)) formed during the reaction should be removed from the reaction liquid as quickly as possible to increase the reaction rate. However, the reaction rate cannot be raised in the process where the ester interchanging reaction is carried out in a reaction vessel having a distillation column disposed at an upper position thereof This is because that the ester interchange reaction of such a process occurs only in the reaction vessel containing the catalyst and that the gas-liquid interface area, through which the low-boiling product is transferred from liquid phase into gas phase by vaporization, is small. Therefore, a sufficient removal of the low-boiling product cannot be attained, thereby failing to shift the equilibrium toward the product side.

On the other hand, in the process of the present invention, the catalyst is widely distributed within the continuous multi-stage distillation column and the ester interchange reaction is allowed to proceed in a region having a large gas-liquid interface area. In this region, the reaction liquid supplied to the column flows downward through the column while being repeatedly brought into gas-liquid contact with the vapor coming up from a lower position of the column, thereby ensuring the continuous distillation of the low-boiling product and the continuous ester interchange reaction. During the downward flow of the reaction liquid, the low-boiling product, alcohol (D), is vaporized from the reaction liquid to the vapor phase. As a result, each component in the continuous multi-stage distillation column has a concentration gradient along the length direction of the column. The concentration of the high-boiling alkyl ester (C) in the reaction liquid gradually increases from the uppermost catalytic stage toward a lower position of the column. The concentration of the low-boiling alcohol (D) in the reaction liquid gradually decreases from the upper position toward the lower position, and may be a very small level near the bottom. In the vapor phase, the concentration of the low-boiling alcohol (D) gradually increases from the lower position toward the upper position of the column.

As described above, in the present invention, the ester interchange reaction proceeds in the continuous multi-stage distillation column. When the reaction at a given position in the reaction zone is considered, the reaction liquid has a composition closed to the equilibrium composition as a result of the reaction, and the vapor phase has a composition approximately in a gas-liquid equilibrium with the reaction liquid. Therefore, the reaction would not proceed any further if the reaction liquid is retained in the given position. However, in the present invention, the reaction liquid flows downward and is repeatedly brought into gas-liquid contact with a vapor phase having a lower concentration of the low-boiling reaction product, i.e., the alcohol (D). Thus, the reaction further proceeds to concentrate the high-boiling alkyl ester (C) of acrylic or methacrylic acid in the reaction liquid.

Since the ester interchange reaction proceeds only in the reaction vessel in the conventional process, the distillation column is merely used to separate the vapor of the low-boiling starting material from the vapor of the low-boiling product, both transferred into the vapor phase via the gas-liquid interface of the reaction vessel, and reflux the condensed low-boiling starting material into the reaction vessel. Therefore, the process of the present invention has the following advantages as compared with the conventional process.

(1) The gas-liquid interface area is extremely large and the material transfer of the low-boiling by-product (alcohol (D)) to the vapor phase is easy.

(2) The reaction liquid flows downward in the continuous multi-stage distillation column while being repeatedly brought into gas-liquid contact with the vapor coming up from the lower position, thereby ensuring the continuous ester interchange reaction. Therefore, the conversion of the starting material increases although the process is a continuous process. On the other hand, it is difficult to increase the conversion of the starting material in the conventional process where the ester interchange reaction is carried out in the reaction vessel and the object compound, alkyl ester (C) of acrylic or methacrylic acid, is continuously taken out from the reaction vessel. No process for continuously carrying out ester interchange reaction has been proposed. To increase the conversion in the conventional process, it is necessary to carry out the batch-wise reaction for a long time.

(3) Since the vapor rises along the continuous multi-stage distillation column while being repeatedly brought into gas-liquid contact with the reaction liquid flowing downward, the heat energy of the vapor is effectively utilized in the reaction and distillation of the low-boiling product.

In the present invention, the catalyst is required to be present in the continuous multi-stage distillation column, preferably the catalyst is disposed on two or more stages of the continuous multi-stage distillation column. When the catalyst is a homogenous catalyst soluble in the reaction liquid under the reaction conditions, the catalyst may be continuously supplied to the distillation column so that the catalyst is present in the reaction system. When the catalyst is a heterogeneous catalyst insoluble in the reaction liquid under the reaction conditions, the solid catalyst is disposed in the distillation column so that the catalyst is present in the reaction system. These two kinds of catalysts may be used in combination.

The homogenous catalyst may be supplied to the distillation column simultaneously with the starting material after mixed with at least one of the starting alkyl ester (A) and the starting alcohol (B), or the catalyst and the starting materials may be respectively supplied to different stages of the column. The catalyst may be supplied to any position so long as at least one stage is included between the supplied position and the bottom of the distillation column. However, since the ester interchange reaction proceeds in a region below the catalyst-supplied position, the catalyst is preferably supplied to a position between the top of the distillation column and the position where the starting materials are supplied.

The heterogeneous catalyst may be packed into any position in the distillation column in a desired amount. It is sufficient that the position having the catalyst has at least one theoretical distillation stage, preferably two or more theoretical distillation stages.

The method of supplying the starting lower alkyl ester (A) and the starting alcohol (B) into the continuous multi-stage distillation column is not particularly limited. Any method may be used so long as the starting materials are brought into contact with the catalyst in at least one stage and preferably two or more stages of the distillation column. The starting materials may be introduced into the same stage of the distillation column or into different stages of the distillation column separately. It is also preferable to continuously supply the higher-boiling alcohol (B) to a stage higher than the stages having the catalyst and continuously supply the lower-boiling alkyl ester (A) to a lower position of the distillation column. In this case, the higher-boiling starting material being supplied to an upper position may contain a small amount of the lower-boiling starting material. Likewise, the lower-boiling starting material being supplied to a lower position may contain a small amount of the higher-boiling starting material. The molar ratio of the alcohol (B) to the alkyl ester (A) supplied to the continuous multi-stage distillation column depends on the kind and the amount of the catalyst and the reaction conditions, and preferably 0.1 to 10.

The low-boiling lower alcohol (D) by-produced during the reaction in the continuous multi-stage distillation column is continuously taken out from the distillation column in a vapor form. The lower alcohol (D) alone may be taken out from the distillation column. When the alcohol (D) and the starting alkyl ester (A) form an azeotrope, the alcohol (D) is taken out with the alkyl ester (A) as an azeotropic composition. The material taken out may contain a small amount of the high-boiling product. The gaseous material such as the alcohol (D) is preferably taken out from the top of the column. In this case, the material may be refluxed at the top of the distillation column to concentrate the low-boiling product.

The alkyl ester (C) produced by the ester interchange reaction is continuously taken out in a liquid form as the high-boiling product from a lower position of the continuous multi-stage distillation column. A high-boiling catalyst soluble in the reaction liquid under the reaction conditions may be also contained, if used, in the liquid taken out from the lower position of the distillation column. The outlet for taking out the alkyl ester (C) is preferably positioned at the bottom of the distillation column.

The amount of the catalyst used in the present invention varies depending on the kind of the catalyst, the kind of the continuous multi-stage distillation column, the kinds and the amount ratio of the starting alkyl ester (A) to the starting alcohol (B) and the reaction conditions such as temperature and pressure. When the homogeneous catalyst is continuously supplied to the reaction zone in the continuous multi-stage distillation column, the catalyst is generally used in an amount of 0.0001 to 50% by weight of the total weight of the starting alkyl ester (A) and the starting alcohol (B) being supplied. When the catalyst is a heterogeneous solid catalyst placed in the continuous multi-stage distillation column, the amount is preferably 0.01 to 75% by volume of the void volume of the column.

In the present invention, the ester interchange reaction takes place in the continuous multi-stage distillation column having the catalyst. Therefore, the amount of the reaction product generally depends on the hold-up of the distillation column. When distillation columns having the same height and diameter are compared, a distillation column having a greater hold-up is preferable due to a longer residence time of the reaction liquid, i.e., a longer reaction time. However, when the hold-up is excessively great, side reactions and flooding are likely to occur due to the increased residence time. Therefore, the hold-up of the distillation column in the present invention is generally 0.005 to 0.75 in terms of the volume ratio of the hold-up volume to the void volume of the continuous multi-stage distillation column, although the hold-up varies depending on the distillation conditions and the kind of the distillation column.

In the present invention, the average residence time of the reaction liquid in the continuous multi-stage distillation column depends on the reaction conditions and the kind and the inner structure, such as the kinds of the plate and packing, of the multi-stage distillation column, and generally 0.01 to 10 hours, preferably 0.05 to 5 hours. The reaction temperature, namely the temperature inside the continuous multi-stage distillation column depends on the kind of the starting lower alkyl ester (A) and the starting higher alcohol (B), and preferably 30 to 150° C., more preferably 60 to 140° C. The pressure may be the atmospheric pressure or a reduced pressure.

In the present invention, although the use of a solvent is not necessarily required, an inert solvent such as an ether, an aliphatic hydrocarbon, an aromatic hydrocarbon, a halogenated aliphatic hydrocarbon or a halogenated aromatic hydrocarbon may be suitably used to facilitate the reaction operations or for other purposes. Particularly preferred are hexane, benzene and cyclohexane due to their ability of forming an azeotrope with the alcohol (D) formed by the ester interchange reaction and their inertness to the reaction. An inert gas such as nitrogen, helium and argon may be present in the reaction system. Also, an inert gas or a gaseous, low-boiling organic compound inert to the reaction may be introduced from a lower position of the continuous multi-stage distillation column to accelerate the removal of the low-boiling alcohol (D) by-produced during the reaction. Oxygen or air may be present in the reaction system to suppress polymerization.

The present invention will be described more specifically while referring to the reaction apparatus shown in the drawings, but the present invention is not intended to be limited thereto.

As shown in FIG. 1, a starting mixture of the alkyl ester (A) and the alcohol (B) is introduced into a continuous multi-stage distillation column 1 equipped with a reboiler 5 and a condenser 4 via an inlet pipe 2 through a preheater 3. The reaction-distillation is carried out by heating the liquid at the bottom of the distillation column by the reboiler 5. The liquid component containing the high-boiling alkyl ester (C) produced in the continuous multi-stage distillation column in the presence of a catalyst is continuously taken out as the bottom liquid from an outlet pipe 6. The vapor component containing a low-boiling alcohol (D) is continuously taken out as the top gas, condensed in the condenser 4 and taken out as the top liquid via an outlet pipe 7. A part of the top liquid may be refluxed to an upper position of the continuous multi-stage distillation column.

Figure 2:
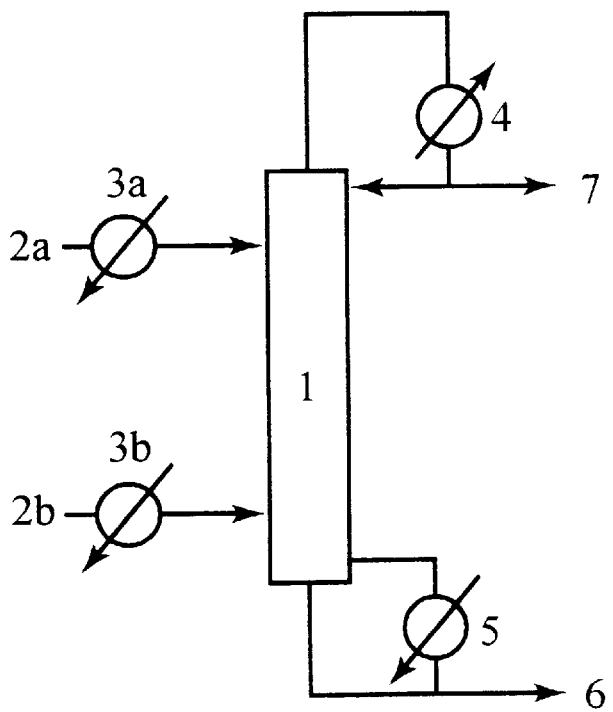
FIG. 2 is a flow sheet showing another process of the present invention where a low-boiling starting material and a high-boiling starting material are separately introduced into respective upper and lower stages of a continuous multi-stage distillation column.

Alternatively, as shown in FIG. 2, a higher-boiling starting material between the alkyl ester (A) and the alcohol (B), generally the alcohol (B), is introduced into a continuous multi-stage distillation column 1 via an inlet pipe 2a through a preheater 3a. Separately, a lower-boiling one, generally the alkyl ester (A), is introduced into a preheater 3b for vaporization via an inlet pipe 2b, vaporized therein and then continuously introduced into the continuous multi-stage distillation column from a lower position thereof Thus, the reaction-distillation takes place. The liquid component containing the high-boiling alkyl ester (C) produced in the continuous multi-stage distillation column in the presence of a catalyst is continuously taken out as the bottom liquid from an outlet pipe 6. The vapor component containing the low-boiling alcohol (D) is continuously taken out as the top gas, condensed in the condenser 4 and taken out as the top liquid via an outlet pipe 7. A part of the top liquid may be refluxed to an upper position of the continuous multi-stage distillation column.

The present invention will be described more specifically with reference to following examples. However, it should be construed that the present invention is not limited thereto.

EXAMPLE 1

A continuous multi-stage distillation column 1 (height: 1150 mm; diameter: 20 mm) as schematically shown in FIG.

1 was packed with Dickson packings (3 mm diameter) made of stainless steel. From an inlet pipe 2 through a preheater 3 positioned 40 cm below the top of the column 1, a liquid mixture was continuously supplied to the distillation column 1 at a flow rate of 88.52 g/hour. The liquid mixture had a composition of 61.00% by weight of methyl methacrylate (MMA), 38.41% by weight of n-butanol (n-BuOH), 0.58% by weight of tetra-n-butoxytitanium (Ti(OBu)$_4$) as the catalyst and 0.01% by weight of hydroquinone monomethyl ether (MQ) as the polymerization inhibitor. The heat necessary for continuing the reaction-distillation was supplied by heating a liquid at a lower position of the column. During the operation, air was supplied from the bottom of the column at a flow rate of 10 ml/minute.

As the result of the reaction, a liquid containing the catalyst component and the reaction product of n-butyl methacrylate (BMA) was obtained from the bottom at a rate of 74.15 g/hour via an outlet pipe 6. The composition of the obtained liquid was 18.06% by weight of MMA, 7.33% by weight of n-BuOH, 73.17% by weight of BMA, 0.69% by weight of Ti(OBu)$_4$, 0.01% by weight of MQ and 0.74% by weight of a high-boiling by-product. The effluent gas from an outlet pipe at the top of the distillation column 1 was condensed in a condenser 4, and a part of the condensed liquid was taken out via an outlet pipe 7 at a reflux ratio of 1. From the condensed liquid, an azeotropic mixture of methanol (MeOH) as the low-boiling product and methyl methacrylate was obtained at a rate of 14.39 g/hour. The composition of the azeotropic mixture was 85.84% by weight of MeOH, 14.12% by weight of MMA, 0.04% by weight of n-BuOH and 0.002% by weight of BMA. The temperature at the bottom of the distillation column was 108° C. during the reaction. The hold-up weight of the distillation column measured after the reaction was 17.3 g.

The conversion of methyl methacrylate was 71.4% and the conversion of n-butanol was 84.0%. The selectivity of n-butyl methacrylate was 99.0% based on MMA.

COMPARATIVE EXAMPLE 1

Into a 1 liter flask equipped with a stirrer, a thermometer, a packed distillation column (height: 300 mm; diameter: 20 mm; packed with Dickson packings (3 mm diameter) made of stainless steel) having a top fractionating column, and an air inlet tube, were charged all at once 244.0 g of methyl methacrylate (MMA), 153.6 g of n-butanol (n-BuOH), 2.32 g of tetra-n-butoxytitanium (Ti(OBu)$_4$) and 40 mg of hydroquinone monomethyl ether (MQ). The contents were stirred under a stream of air for 2 hours to carry out the ester interchange reaction. During the reaction, a fraction was taken out from the top of the distillation column at a reflux ratio of 1 to 5 so that the temperature at the top was kept at 65° C. or lower. During the reaction, the temperature in the flask increased from 95° C. to 130° C.

After 2-hout reaction, was obtained 71.9g of a top liquid having a composition of 69.37% by weight of MeOH, 29.75% by weight of MMA, 0.63% by weight of n-BuOH and 0.25% by weight of BMA. The residual liquid in the flask weighed 328.1 g and had a composition of 1.00% by weight of MeOH, 12.10% by weight of MMA, 7.31% by weight of n-BuOH, 74.67% by weight of BMA and 4.89% by weight of other components. The conversion of methyl methacrylate was 75.0% and the conversion of n-butanol was 84.0%. The selectivity of n-butyl methacrylate was 94.0% based on MMA.

EXAMPLE 2

Using the same apparatus as used in Example 1, a liquid mixture of 53.47% by weight of methyl methacrylate (MMA), 45.51% by weight of n-butanol (n-BuOH), 1.01% by weight of tetra-n-butoxytitanium (Ti(OBu)$_4$) as the catalyst and 0.01% by weight of hydroquinone monomethyl ether (MQ) as the polymerization inhibitor was continuously supplied to the distillation column 1 at a flow rate of 100.99 g/hour from the inlet pipe 2 through the preheater 3. During the reaction, air was supplied from the bottom at a flow rate of 10 ml/minute.

As the result of the reaction, a liquid containing the catalyst component and n-butyl methacrylate (BMA) as the reaction product was obtained from the bottom at a rate of 85.06 g/hour via the outlet pipe 6. The composition of the obtained liquid was 4.01% by weight of MMA, 14.53% by weight of n-BuOH, 79.45% by weight of BMA, 1.20% by weight of Ti(OBu)$_4$, 0.01% by weight of MQ and 0.80% by weight of a high-boiling by-product. The effluent gas from an outlet pipe at the top of the distillation column was condensed in the condenser 4 and a portion of the condensed liquid was taken out via the outlet pipe 7 at a reflux ratio of 1. From the condensed liquid, an azeotropic mixture of methanol as the low-boiling product and methyl methacrylate was obtained at a rate of 17.95 g/hour. The composition thereof was 85.72% by weight of MeOH, 14.10% by weight of MMA, 0.12% by weight of n-BuOH and 0.06% by weight of BMA. The temperature at the bottom was 116° C. during the reaction. The hold-up weight of the distillation column measured after the reaction was 18.3 g.

The conversion of methyl methacrylate was 89.0% and the conversion of n-butanol was 77.4%. The selectivity of n-butyl methacrylate was 99.0% based on MMA.

EXAMPLE 3

A continuous multi-stage distillation column 1 (height: 1700 mm; diameter: 20 mm) as schematically shown in FIG. 2 was packed with Dickson packings (3 mm diameter) made of stainless steel. A liquid mixture of 98.50% by weight of n-butanol (n-BuOH), 1.48% by weight of tetra-n-butoxytitanium (Ti(OBu)$_4$) as the catalyst and 0.02% by weight of hydroquinone monomethyl ether (MQ) as the polymerization inhibitor was continuously supplied to the distillation column 1 at a position 40 mm below the top thereof at a flow rate of 34.52 g/hour via an inlet pipe (2a) through a preheater 3a. Separately, a gaseous methyl methacrylate (MMA) was continuously supplied to the distillation column 1 at a position 132 mm below the top thereof at a flow rate of 54.00 g/hour via an inlet pipe 2b through a preheater 3b for vaporization. The heat necessary for continuing the reaction-distillation was supplied by heating a liquid at a lower position of the column. During the operation, air was supplied from the bottom at a flow rate of 10 ml/minute.

As the result of the reaction, a liquid containing the catalyst component and n-butyl methacrylate (BMA) as the reaction product was obtained from the bottom at a rate of 72.55 g/hour via the outlet pipe 6. The composition of the obtained liquid was 12.46% by weight of MMA, 3.27% by weight of n-BuOH, 82.80% by weight of BMA, 0.70% by weight of Ti(OBu)$_4$, 0.01% by weight of MQ and 0.76% by weight of a high-boiling by-product. The effluent gas from an outlet pipe at the top was condensed in the condenser 4 and a part of the condensed liquid was taken out via the outlet pipe 7 at a reflux ratio of 3. From the condensed liquid, an azeotropic mixture of methanol as the low-boiling product and methyl methacrylate was obtained at a rate of 15.93 g/hour. The composition thereof was 85.84% by weight of MeOH, 14.12% by weight of MMA, 0.04% by weight of n-BuOH and 0.002% by weight of BMA. The temperature at the bottom was 120° C. during the operation. The hold-up weight of the distillation column measured after the reaction was 25.3 g.

The conversion of methyl methacrylate was 79.1% and the conversion of n-butanol was 93.0%. The selectivity of n-butyl methacrylate was 99.0% based on MMA.

EXAMPLE 4

Using the same apparatus as used in Example 3, a liquid mixture of 98.38% by weight of n-butanol (n-BuOH), 1.60% by weight of tetra-n-butoxytitanium (Ti(OBu)$_4$) as the catalyst and 0.02% by weight of hydroquinone monomethyl ether (MQ) as the polymerization inhibitor was continuously supplied to the distillation column 1 at a flow rate of 46.76 g/hour via the inlet pipe 2a through the preheater 3a. Separately, a gaseous methyl methacrylate (MMA) was continuously supplied to the distillation column 1 at a flow rate of 54.00 g/hour via the inlet pipe 2b through the preheater 3b for vaporization. During the reaction, air was supplied from the bottom at a flow rate of 10 ml/minute.

As the result of the reaction, a liquid containing the catalyst and n-butyl methacrylate (BMA) as the reaction product was obtained from the bottom at a rate of 81.61 g/hour via the outlet pipe 6. The composition of the obtained liquid was 0.70% by weight of MMA, 10.32% by weight of n-BuOH, 87.47% by weight of BMA, 0.63% by weight of Ti(OBu)$_4$, 0.01% by weight of MQ and 0.88% by weight of a high-boiling by-product. The effluent gas from an outlet pipe at the top was condensed in the condenser 4 and a part of the condensed liquid was taken out via the outlet pipe 7 at a reflux ratio of 2.5. From the condensed liquid, an azeotropic mixture of methanol as the low-boiling product and methyl methacrylate was obtained at a rate of 18.93 g/hour. The composition was 85.85% by weight of MeOH, 14.12% by weight of MMA, 0.03% by weight of n-BuOH and 0.002% by weight of BMA. The temperature at the bottom was 129° C. during the reaction. The hold-up weight of the distillation column measured after the reaction was 29.7 g.

The conversion of methyl methacrylate was 94.0% and the conversion of n-butanol was 81.7%. The selectivity of n-butyl methacrylate was 99.0% based on MMA.

As described above, according to the present invention, the target alkyl ester of acrylic or methacrylic acid can be continuously produced by ester interchange reaction in a high yield, a high conversion and a high selectivity.

What is claimed is:

1. A process for continuously producing an alkyl ester of acrylic or methacrylic acid by ester interchange reaction represented by the following reaction scheme:

wherein R$^1$ is hydrogen or methyl, R$^2$ is an alkyl having 1 to 6 carbon atoms, R$^3$ is an alkyl having 2 to 20 carbon atoms or a mono- or polyhydroxyalkyl having 2 to 20 carbon atoms such that R$^2$OH has a boiling point lower than that of R$^3$OH, the process comprising the steps of:

supplying the starting alkyl ester:

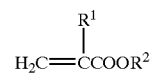

and the starting alcohol R$^3$OH to a continuous multi-stage distillation column, having a top, as starting materials;

bringing the starting materials into contact with a catalyst in the distillation column to allow the ester interchange reaction to take place between the starting materials while continuously taking out the by-produced alcohol R$^2$OH in a vapor form from the top of the distillation column, by distillation; and continuously taking out the resultant alkyl ester of acrylic or methacrylic acid

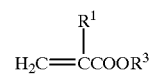

in a liquid form from a lower position of the distillation column.

2. The process according to claim 1, wherein the catalyst is a homogeneous catalyst, which is continuously supplied to the continuous multi-stage distillation column so that the catalyst is present in the distillation column.

3. The process according to claim 1, wherein the homogeneous catalyst is a complex of titanium.

4. The process according to claim 1, wherein the catalyst is a heterogeneous catalyst, which is placed in the continuous multi-stage distillation column so that solid catalyst is present in the distillation column.

5. The process according to claim 1, wherein the starting alkyl ester is methyl methacrylate, and the starting alcohol is 1-butanol or 2-butanol.

6. The process according to claim 5, wherein the catalyst is a homogeneous catalyst, which is continuously supplied to the continuous multi-stage distillation column so that the catalyst is present in the distillation column.

7. The process according to claim 6, wherein the homogeneous catalyst is a complex of titanium.

8. The process according to claim 5, wherein the catalyst is a heterogeneous catalyst, which is placed in the continuous multi-stage distillation column so that solid catalyst is present in the distillation column.

9. The process according to claim 1, wherein the catalyst is provided on at least two stages of the continuous multi-stage distillation column.

10. The process according to claim 2, wherein the homogeneous catalyst is supplied to the distillation column at a location between the top of the distillation column and positions where the starting materials are supplied to the distillation column.

11. The process according to claim 1, wherein the starting alcohol has a higher boiling point than that of the starting alkyl ester, and is supplied to the distillation column at a higher stage than a stage to which the starting alkyl ester is supplied.

12. The process according to claim 11, wherein the starting alcohol is fed to the distillation column at a higher stage than stages having the catalyst.

13. The process according to claim 1, wherein the ester interchange reaction is allowed to take place in a plurality of stages of the continuous multi-stage distillation column.

* * * * *